(12) United States Patent
Kolenbrander et al.

(10) Patent No.: US 9,435,736 B2
(45) Date of Patent: Sep. 6, 2016

(54) SYSTEM FOR BLOOD SEPARATION WITH SHIELDED EXTRACTION PORT AND OPTICAL CONTROL

(71) Applicant: Terumo BCT, Inc., Lakewood, CO (US)

(72) Inventors: Jeremy P. Kolenbrander, Brighton, CO (US); Brian M. Holmes, Evergreen, CO (US); Thomas J. Felt, Boulder, CO (US); James R. Ladtkow, Broomfield, CO (US)

(73) Assignee: Terumo BCT, Inc., Lakewood, CO (US)

( * ) Notice: Subject to any disclaimer, the term of this patent is extended or adjusted under 35 U.S.C. 154(b) by 423 days.

(21) Appl. No.: 14/014,147

(22) Filed: Aug. 29, 2013

(65) Prior Publication Data

US 2014/0005023 A1 Jan. 2, 2014

Related U.S. Application Data

(62) Division of application No. 12/959,987, filed on Dec. 3, 2010, now Pat. No. 8,535,210.

(60) Provisional application No. 61/285,597, filed on Dec. 11, 2009.

(51) Int. Cl.
*A61M 1/36* (2006.01)
*G01N 21/51* (2006.01)
(Continued)

(52) U.S. Cl.
CPC ............ *G01N 21/51* (2013.01); *A61M 1/3693* (2013.01); *A61M 1/3696* (2014.02); *B04B 13/00* (2013.01);
(Continued)

(58) Field of Classification Search
CPC ............ A61M 1/3693; A61M 1/3696; A61M 2205/3306; B04B 2013/006; B04B 5/0442; B04B 5/0471; B04B 5/0492
See application file for complete search history.

(56) References Cited

U.S. PATENT DOCUMENTS 4,151,844 A 5/1979 Cullis et al.
4,493,691 A 1/1985 Calari
(Continued)

FOREIGN PATENT DOCUMENTS

DE 3413065 A1 10/1984
DE 3301113 C2 1/1985
EP 0392475 A2 10/1990

OTHER PUBLICATIONS

International Search Report and Written Opion, PCT/US2010/058917, Feb. 23, 2011.
(Continued)

*Primary Examiner* — Timothy Cleveland
(74) *Attorney, Agent, or Firm* — John R. Merkling; Elizabeth J. Reagan; René A. Pereyra

(57) ABSTRACT

A centrifugal blood separation system comprising a rotor, a light source, an optical sensor, a control system, a separation vessel, and an optical cell on the separation vessel. The optical cell has a first extraction port extending radially outwardly into the optical cell, a red blood cell extraction port downstream from the first extraction port and extending into the optical cell beyond the first extraction port; and a dam between said first extraction port and said red blood cell extraction port, having an upper edge and a lower edge, wherein the first extraction port and the red cell extraction port are radially between the upper edge and the lower edge of the dam. Also, a first extraction port having a bore having a first diameter, a lumen having a second diameter smaller than the first diameter, and a frustro-conical passageway coupling the bore to the lumen.

3 Claims, 7 Drawing Sheets

(51) Int. Cl.
  *B04B 13/00*   (2006.01)
  *G01N 35/00*   (2006.01)

(52) U.S. Cl.
  CPC .......... *A61M 2202/0439* (2013.01); *A61M 2205/3306* (2013.01); *B04B 2013/006* (2013.01); *G01N 2035/00495* (2013.01)

(56) References Cited

U.S. PATENT DOCUMENTS

| | | |
|---|---|---|
| 4,557,719 A | 12/1985 | Neumann et al. |
| 4,670,002 A | 6/1987 | Koreeda et al. |
| 4,671,102 A | 6/1987 | Vinegar et al. |
| 4,724,317 A | 2/1988 | Brown et al. |
| 4,834,890 A | 5/1989 | Brown et al. |
| 5,076,911 A | 12/1991 | Brown et al. |
| 5,104,526 A | 4/1992 | Brown et al. |
| 5,260,598 A | 11/1993 | Brass et al. |
| 5,316,667 A | 5/1994 | Brown et al. |
| 5,322,620 A | 6/1994 | Brown et al. |
| 5,653,887 A | 8/1997 | Wahl et al. |
| 5,814,279 A | 9/1998 | Biesel et al. |
| 5,948,271 A | 9/1999 | Wardwell et al. |
| 6,053,856 A | 4/2000 | Hlavinka |
| 6,254,784 B1 | 7/2001 | Nayak et al. |
| 6,334,842 B1 | 1/2002 | Hlavinka et al. |
| 6,338,820 B1 | 1/2002 | Hubbard et al. |
| 6,506,606 B1 | 1/2003 | Winkelman et al. |
| 6,514,189 B1 | 2/2003 | Hlavinka et al. |
| 6,632,399 B1 | 10/2003 | Kellogg et al. |
| 6,790,371 B2 | 9/2004 | Dolecek |
| 7,033,512 B2 | 4/2006 | Hlavinka et al. |
| 7,549,956 B2 | 6/2009 | Hlavinka et al. |
| 7,605,388 B2 | 10/2009 | Carter et al. |
| 8,535,210 B2 | 9/2013 | Kolenbrander et al. |
| 2006/0191857 A1* | 8/2006 | Hlavinka ............ A61M 1/3693 494/37 |
| 2007/0102374 A1 | 5/2007 | Kolenbrander |

OTHER PUBLICATIONS

Salgaller, Michael L., "A manifesto on the current state of dendritic cells adoptive immunotherapy", Transfusion, Apr. 2003, pp. 422-424, vol. 43.

* cited by examiner

SYSTEM FOR BLOOD SEPARATION WITH SHIELDED EXTRACTION PORT AND OPTICAL CONTROL

CROSS-REFERENCE TO RELATED APPLICATIONS

This application is related to U.S. Pat. No. 7,605,388, which is incorporated herein by reference. This application is a divisional of U.S. Pat. No. 8,535,210 issued on Sep. 17, 2013, which is a non-provisional of U.S. Provisional Application No. 61/285,597, filed on Dec. 11, 2009.

BACKGROUND OF INVENTION

Blood collection and processing play important roles in the worldwide health care system. In conventional large scale blood collection, blood is removed from a donor or patient, separated into its various blood components via centrifugation, filtration, or elutriation and stored in sterile containers for future infusion into a patient for therapeutic use. The separated blood components typically include fractions comprising red blood cells, white blood cells, platelets, and plasma. Separation of blood into its components can be performed continuously during collection or can be performed subsequent to collection in batches, particularly with respect to the processing of whole blood samples. Separation of blood into its various components under highly sterile conditions is critical to many therapeutic applications.

Recently, apheresis blood collection techniques have been adopted in many large scale blood collection centers wherein a selected component of blood is collected and the balance of the blood is returned to the donor during collection. In apheresis, blood is removed from a donor and immediately separated into its components by on-line blood processing methods. Typically, on-line blood processing is provided by density centrifugation, filtration, or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing platelet-pheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation.

Both conventional blood collection and apheresis systems typically employ differential centrifugation methods for separating blood into its various blood components. In differential centrifugation, blood is circulated through a sterile separation chamber which is rotated at high rotational speeds about a central rotation axis. Rotation of the separation chamber creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887 and U.S. Pat. No. 7,033,512.

To achieve continuous, high throughput blood separation, extraction or collect ports are provided in most separation chambers. Extraction ports are capable of withdrawing material from the separation chamber at adjustable flow rates and, typically, are disposed at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase. For example, if the fraction containing white blood cells resides too close to the extraction port corresponding to platelet enriched plasma, white blood cells may enter the platelet enriched plasma stream exiting the separation chamber, thereby degrading the extent of separation achieved during blood processing. Although conventional blood processing via density centrifugation is capable of efficient separation of individual blood components, the purities of individual components obtained using this method is often not optimal for use in many therapeutic applications.

As a result of the inability to achieve optimal purity levels using centrifugation separation alone, a number of complementary separation techniques based on filtration, elutriation and affinity-based techniques have been developed to achieve the optimal purities needed for use of blood components as therapeutic agents. These techniques, however, often reduce the overall yield realized and may reduce the therapeutic efficacy of the blood components collected. Exemplary methods and devices of blood processing via filtration, elutriation and affinity based methods are described in U.S. Pat. No. 6,334,842.

Centrifugal blood component separation apparatus has been described in commonly assigned U.S. Pat. No. 7,605,388, for instance. As described in U.S. Pat. No. 7,605,388, an optical cell may be configured such that white blood cells can be extracted through a first extraction port, plasma and/or platelets can be extracted through second extraction port, and red blood cells can be extracted through third extraction port. As also mentioned in U.S. Pat. No. 7,605,388 (but not shown), optical cells of separation chambers can include one or more dams positioned proximate to the extraction ports to facilitate selective extraction of separated blood components having reduced impurities arising from adjacent components. The use of dams in blood processing via density centrifugation is known in the art and described in U.S. Pat. Nos. 6,053,856; 6,334,842 and 6,514,189.

SUMMARY OF THE INVENTION

This invention provides methods, devices and device components for improving the processing of fluids comprising fluid components, such as blood, components of blood and fluids derived from blood. Methods, devices and device components of the present invention are capable of monitoring and controlling separation of blood into discrete components and subsequent collection of selected components.

It has been found that certain transient conditions can cause loss of certain blood components, particularly white blood cells, in an optically controlled blood separation apparatus. Improvements to an optical chamber, wherein blood components are extracted from a separation chamber, have been found to improve the efficiency of white blood cell collection.

A function of the centrifuge blood processing system described herein may be the collection of white blood cells. It has been found that the collection of white blood cells is highly sensitive to changing flow conditions. If the pumps controlling fluid flow stop, the interface between the red blood cells and the buffy coat generally falls, at least temporarily, to the level of the red blood cell extraction port. In such circumstances, a layer of white cells that had been collected on top of the red blood cell layer is frequently carried into the red blood cell extraction port and returned to the patient or donor. Since such white cells are co-mingled with the total blood volume of the patient/donor, they are no longer available for collection without significant re-processing of the patient's blood. Such losses can significantly decrease the efficiency of white blood cell collection.

According to the present invention, the optical cell of the separation vessel comprises at least a buffy coat extraction port and a red blood cell extraction port. White cells collect at the buffy coat extraction port. A ramp, a dam and a shield direct white blood cells towards the buffy coat extraction port. The shield leaves a small gap adjacent the buffy coat extraction port. The red blood cell extraction port extends into the optical cell a sufficient radial distance from the axis of rotation along a separation axis such that an orifice lies between the top of the shield and the ramp, as measured radially from the axis of rotation along a separation axis.

This configuration allows white cell-containing buffy coat to be withdrawn from the optical cell through the buffy coat extraction port for further separation in a fluidized-bed filtration chamber. If the flow conditions are interrupted, for example, by stopping one or more of the pumps, the RBC level falls to the level of the orifice of the RBC extraction port. The dam and ramp, however, prevent the buffy coat layer and white cells from flowing downstream to the third extraction port, thus preserving the white cells for collection when steady state flow conditions are re-established.

A further feature of the optical cell reduces false detection of red blood cells in the first extraction port, a condition that might cause a loss of collectable white cells. An extraction port comprised a stepped lumen having a larger diameter bore radially outwardly and a smaller diameter bore radially inwardly. The larger diameter bore is needed to allow for a sufficiently large area for optical detection of conditions in flux monitoring regions. The smaller diameter lumen is needed to promote a higher flow velocity through a white cell tube. The volume of white cells collected is comparatively small, compared to the volumes of red blood cells or plasma being processed through the system. A narrow lumen in the white cell tube reduces the possibility of stagnation in the white cell line. Nevertheless, it is believed that vortices in the fluid flowing through the lumen in a prior art design may temporarily capture white blood cells. White cells may continue to accumulate in the vicinity of a lip until a critical volume is dislodged and passes through the small diameter area of the lumen. The accumulation of white cells near the flux monitoring regions impedes the transmission of light through the flux monitoring regions. The darkening of these regions may be erroneously interpreted as red blood cells. To alleviate this condition, a lumen or bore in the first extraction port has a frustroconical taper.

A feature of the present apparatus may comprise an optical cell for a separation chamber of a density centrifuge blood processing system for separating fluid components, the optical cell being adapted to be mounted on a rotor of said blood processing system, the optical cell comprising an extraction chamber adapted to transmit at least a portion of an incident optical beam; a first extraction port extending radially outwardly into said optical cell with respect to an axis of rotation of the rotor and being adapted to transmit at least a portion of the incident optical beam, the first extraction port having a bore for passing fluid components and an orifice; a red blood cell extraction port downstream from said first extraction port with respect to fluid flowing through the optical cell and having an orifice extending radially outwardly into the optical cell beyond the orifice of the first extraction port; a dam between said first extraction port and said red blood cell extraction port, the dam being generally perpendicular to fluid flowing through said optical cell, and having an upper edge and a lower edge, the lower edge being radially outward from the upper edge, wherein the orifice of the first extraction port and the orifice of the red cell extraction port are radially between the upper edge and the lower edge of the dam.

Another object of the invention may be to provide an optical cell with a fluid passageway placed radially outward from a dam.

Yet another object of the invention may be to provide an optical cell with a ramp at a lower edge of a dam, the ramp extending from the dam upstream beyond a first extraction port. The ramp may extend outwardly from a junction between the ramp and the dam. The ramp may be substantially planar.

Another object or feature may be an optical cell having a plate adjacent an orifice of a first extraction port, the plate being spaced away from the orifice.

In another aspect of the apparatus, an optical cell may have a dam that slants from an upstream position adjacent a wall of the optical cell to a downstream position adjacent a first extraction port.

Another aspect of the apparatus may comprise an extraction port having a bore in fluid communication with an orifice of the extraction port, the bore having a first diameter, a lumen having a second diameter smaller than said first diameter, and a frustro-conical passageway coupling the bore to the lumen.

These and other features and advantages of the invention will be apparent from the following description, drawings and claims.

DETAILED DESCRIPTION OF THE INVENTION

Figure 1:
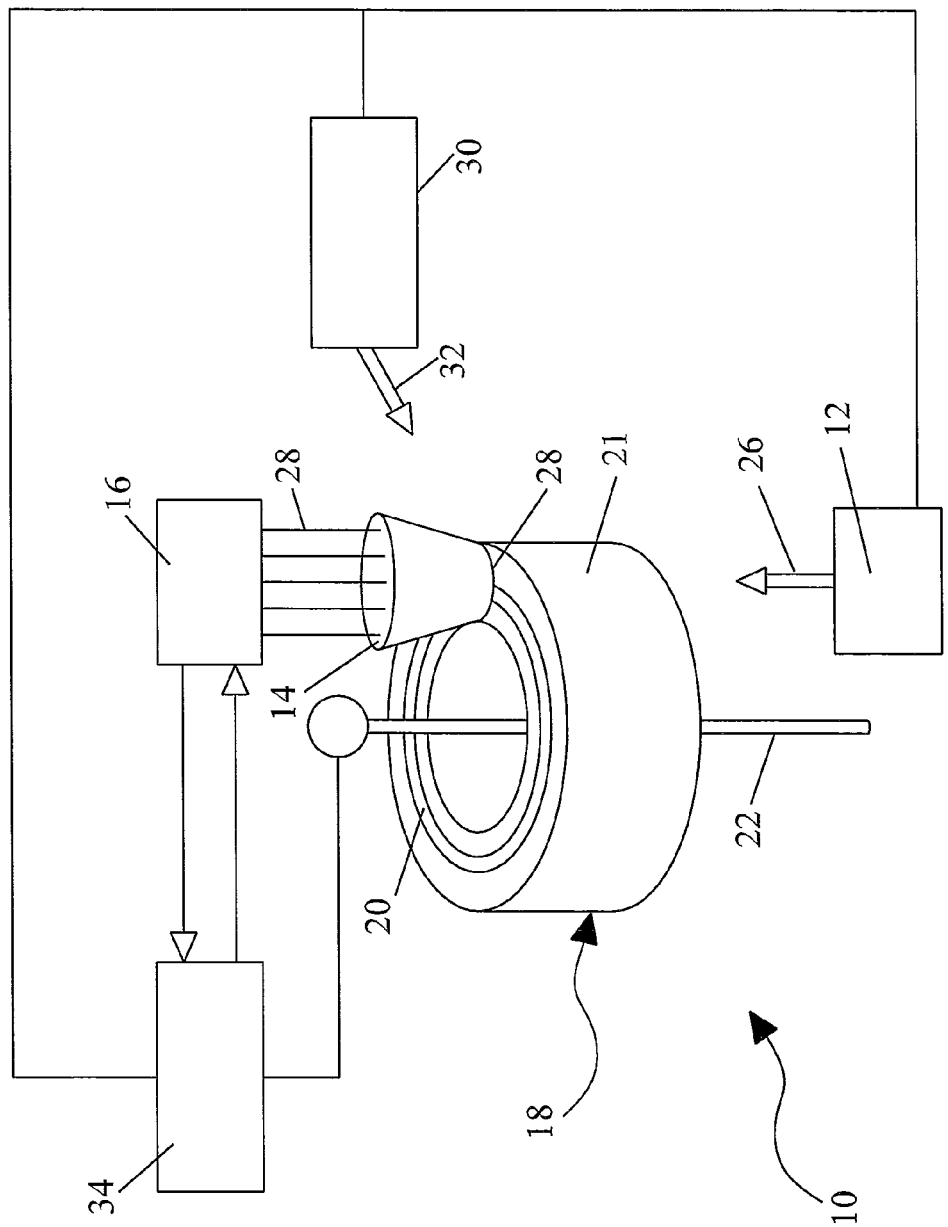
FIG. 1 is a schematic drawing of a centrifuge blood separation apparatus with an optical monitoring and control system.

Referring to the drawings, like numerals indicate like elements and the same number appearing in more than one drawing refers to the same element. In addition, hereinafter, the following definitions apply:

The terms "light" and "electromagnetic radiation" are used synonymously. Light useful for the present invention includes gamma rays, X-rays, ultraviolet light, visible light, infrared light, microwaves, radio waves or any combination of these.

"Separation axis" refers to the axis along which blood components having different densities are separated in a density centrifuge. As a separation chamber is rotated about a central rotation axis in a density centrifuge, the centrifugal force is directed along separation axes. Accordingly, a plurality of axes rotates about the central rotation axis of a density centrifuge.

FIG. 1 schematically illustrates an exemplary embodiment of a blood component separation device 10 with an optical monitoring system capable of measuring a light intensities corresponding to patterns of light originating from an observation region on a separation chamber. The illustrated separation device 10 comprises light source 12, light collection element 14, and two-dimensional detector 16. Light source 12 is in optical communication with a density centrifuge 18 comprising a separation chamber 20 which rotates about central rotation axis 22. Rotation about central rotation axis 22 results in separation of a blood sample in the separation chamber into discrete blood components along a plurality of rotating separation axes oriented orthogonal to the central rotation axis 22. In a preferred embodiment, separation chamber 20 is held in an internal, circular groove in a rotor 24 wherein the separation chamber 20 is positioned and fastened. During operation of the density centrifuge, the rotor is operationally connected to a rotating means such that both rotor and separation chamber are rotated about the central rotation axis 22. In the schematic shown in FIG. 1, the blood sample is separated into an outer higher density phase corresponding to a red blood cell component, an intermediate density phase corresponding to a white blood cell and platelet-containing component (e.g. buffy coat) and a lower density inner phase corresponding to a platelet enriched plasma component.

Light source 12 provides incident light beam 26, which illuminates an observation region 28 on separation chamber 20. In one embodiment, light source 12 is capable of generating an incident light beam, a portion of which is transmitted through at least one blood component undergoing separation in separation chamber 20. At least a portion of scattered or transmitted light 28 from the observation region 28 is collected by light collection element 14. Light collection element 14 is capable of directing at least a portion of the collected light 28 onto two-dimensional detector 16, e.g., a digital camera. The two-dimensional detector 16 detects patterns of scattered and/or transmitted light 28 from the observation region. In an exemplary embodiment, two-dimensional distributions of light intensities comprise images corresponding to patterns of light originating from the observation region 28. In one embodiment, images of the present invention are monochrome images, which provide a measurement of the brightness of separated blood components along the separation axis. Alternatively, images of the present invention are color images, which provide a measurement of the colors of separated blood components along the separation axis.

Observation region 28 is positioned on a portion of the density centrifuge 18, preferably on the separation chamber 20. In the exemplary embodiment illustrated in FIG. 1, separated blood components and phase boundaries between optically differentiable blood components are viewable in observation region 28. In one embodiment, the observation region is positioned on an optical cell of the separation chamber having windows for transmitting the incident beam through the blood sample undergoing processing. In an alternative preferred embodiment, one or more extraction ports (not shown in FIG. 1) are viewable in observation region 28. In another embodiment, observation region 28 is positioned on the top of the separation chamber 20 such that leaks of the blood sample and/or improper alignment of the separation chamber or filler are viewable. In another alternative embodiment, the observation region 28 is positioned on a portion of the separation chamber such that the composition of a separated blood component can be directly monitored. For example, a monitoring system of the present invention provides a method of characterizing the type of cellular component collected and counting the amount of cells extracted from the separation chamber as a function of time. Alternatively, the monitoring system is arranged such that the concentration of non-cellular blood components, such as blood plasma proteins, is directly measured. In one embodiment, the observation region 28 is arranged such that a plurality of measurements are obtained from every measured two-dimensional distribution of scattered and/or transmitted light intensities.

Optionally, the observation region 28 can also be illuminated by light source 30, which is positioned on the same side of the separation chamber as the light collection element and two-dimensional detector. Light source 30 is positioned such that it generates an incident beam 32 which is scattered by the blood sample and/or centrifuge. A portion of the light from light source 30 scattered by the separation chamber and is collected by light collection element 14 and detected by detector 16. The detector 16 is also capable of generating output signals corresponding to light intensities or images. In the exemplary embodiment shown in FIG. 1, two-dimensional detector 16 is operationally connected to a centrifugation device controller 34 capable of receiving the output signals. The device controller 34 displays the measured intensity distributions, stores the measured intensity distributions, processes measured intensity distributions in real time, transmits control signals to various optical and mechanical components of the monitoring system and centrifuge or any combination of these. The device controller 34 is operationally connected to centrifuge 18 and is capable of adjusting selected operating conditions of the centrifuge, such as the flow rates of cellular and non-cellular components out of the separation chamber, the position of one or more phase boundaries along the separation axes, rotational velocity of the separation chamber about central rotation axis 22, the infusion of anticoagulation agents or other blood processing agents to the blood sample, or any combination of these.

As shown in FIG. 1, the controller 34 can also be operationally connected to light source 12 or epi-illumination light source 30. In this embodiment, the device controller 34 and/or detector 16 are capable of generating output signals for controlling illumination conditions. For example, output signals from a detector can be used to control the timing of illumination pulses, illumination intensities, the distribution of illumination wavelengths, or the position of light source 10 or of the epi-illumination light source 30. As also shown in the embodiment illustrated in FIG. 1, centrifugation device controller and two-dimensional detector are in two way communication. In this embodiment, the device controller sends control signals to the detector 16 to selectively adjust detector exposure time, detector gain and to switch between monochrome and color imaging.

Figure 2:
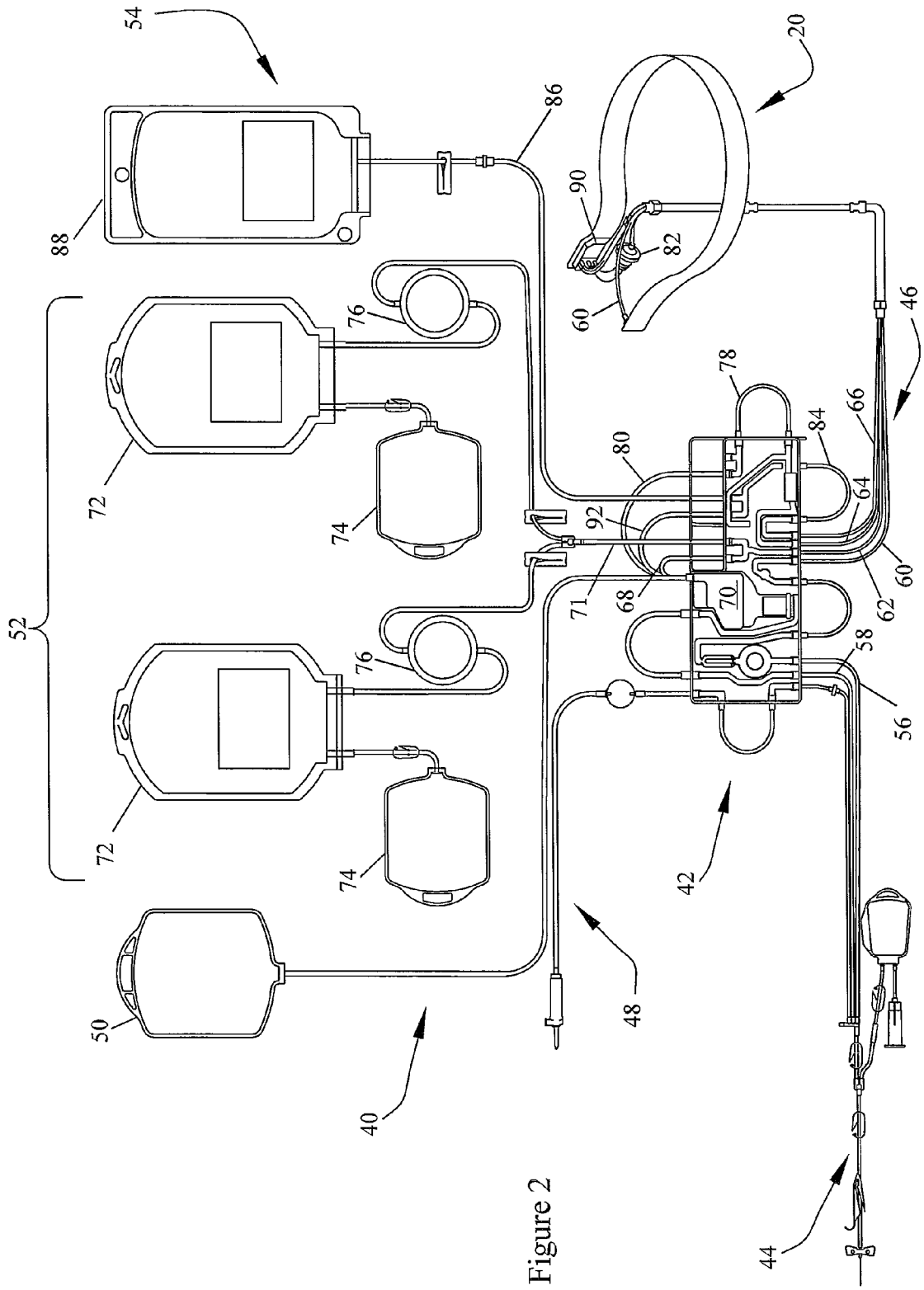
FIG. 2 is a plan view of a blood component separation vessel and tubing set.

The separation chamber 20 and an associated blood component bag and tubing set 40 are illustrated in FIG. 2. The bag and tubing set 40 is intended for single-use, that is, the separation chamber and tubing set are disposable after use with a single donor. The pre-connected extracorporeal tubing set 40 may include a cassette assembly 42 and a number of tubing/collection assemblies 44, 46, 48, 50, 52, and 54 interconnected therewith. Preferably, a blood removal/return tubing assembly 44 provides a single needle interface between a donor and the remainder of the tubing set 40 (although a two-needle set-up may also be used, not shown). At least two lines 56, 58 are provided in assembly 44 for removal of blood from and return of components to the donor. This embodiment includes a cassette assembly 42, which is interconnected between the tubing assembly 44, which connects the donor thereto, and blood inlet/blood component outlet tubing line sub-assembly 46, which provides the interface between cassette assembly 42 and blood processing separation vessel 20. Four tubing lines 60, 62, 64 and 66 are shown in FIG. 2 for transport of blood and components to and from the processing vessel 12. An anticoagulant tubing assembly 48, a vent bag tubing line sub-assembly 50, a red blood cell collection assembly 52, and a white blood cell assembly 54 are also interconnected with cassette assembly 42 in this embodiment. As will be appreciated, the extracorporeal tubing circuit or set 40 and blood processing vessel 20 are preferably pre-interconnected to yield a closed, pre-sterilized disposable assembly for a single use.

Emanating from vessel 20 is an RBC outlet tubing line 62 of the blood inlet/blood component tubing assembly 46 which is interconnected through passageways of cassette 54 assembly 42 with RBC return tubing loop 68 to return separated RBCs to a donor or collection. For return, the RBC return tubing loop 68 is preferably interconnected to the top of a blood return reservoir 70 of the cassette assembly 42. For collection, an RBC collection tubing assembly 52 is provided. RBC collection assembly 52 preferably includes RBC collector tubing line 71 which communicates with one or more RBC collection reservoirs or bags 72, and air removal bags 74. Blood filters 76 may also be provided to remove residual blood components, such as white cells.

In a portion of the cassette assembly 42, plasma tubing 64 of blood inlet/blood tip component tubing assembly 46 interconnects with a pump-engaging, plasma tubing loop 78 and a plasma return tubing loop 80. If collection of plasma is desired, a plasma collect bag (not shown) may also be provided. The plasma return tubing loop 80 returns plasma to donor/patient. For such purpose, the plasma return tubing loop 80 is interconnected to the top of the blood return reservoir 70 of the cassette assembly 42. One or more types of uncollected blood components, e.g., red blood cells, plasma or platelets, collectively referred to as return blood components, will cyclically accumulate in and be removed from reservoir 70 during use.

Like the other separated blood components such as plasma or red blood cells, white blood cells, the principal blood component collected in the present configuration, flow out of the separation chamber 20 through an optical cell 90, which will be more particularly described below. White blood cells are accumulated in a filtration chamber 82 and are periodically emptied into white cell tube 66. At appropriate intervals, the white cells are pumped through a pump loop 84 and a tubing line 86 to a white cell collection bag 88. Alternatively, excess blood component could be returned to the donor through loop 92, which is coupled to the blood return reservoir 70.

The cassette assembly 42 in the embodiment of FIG. 2, may be mounted upon and operatively interface with a pump/valve/sensor assembly of the blood component separation device 10 during use. Further details of an apheresis system set-up including the loading and interaction of a disposable assembly 40 with a blood component separation device 10, may be found in U.S. Pat. No. 5,653,887; U.S. Pat. No. 5,676,644; U.S. Pat. No. 5,702,357; U.S. Pat. No. 5,720,716; U.S. Pat. No. 5,722,946; U.S. Pat. No. 5,738,644; U.S. Pat. No. 5,750,025; U.S. Pat. No. 5,795,317; U.S. Pat. No. 5,837,150; U.S. Pat. No. 5,919,154; U.S. Pat. No. 5,921,950; U.S. Pat. No. 5,941,842; and U.S. Pat. No. 6,129,656, inter alia, and are not exhaustively repeated here.

Figure 3:
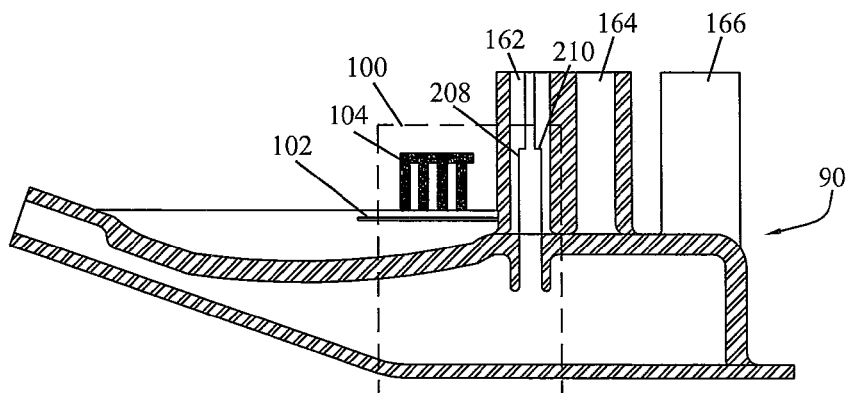
FIG. 3 is a section view of an optical cell of a separation chamber.

FIG. 3 is a top plan view of a prior art optical cell 90 of a separation chamber as described in U.S. Pat. No. 7,605, 388. The device 10 of FIG. 1 acts to produce an observation area 100 that captures images of the optical cell 90 as the optical cell passes under the light collection element 14. Visible in observation area 100 is a first calibration marker comprising an edge 102 of the optical cell and a second calibration marker 104 comprising a series of bars 1 mm in thickness and having a known absorption and scattering characteristics. First and second calibration markers provide references for optimizing focusing of the light collection element, indicating the positions and physical dimensions of portions of a phase boundary monitoring region and measuring the positions of phase boundaries between the red blood cell containing component, the buffy layer and the plasma component.

Figure 4:
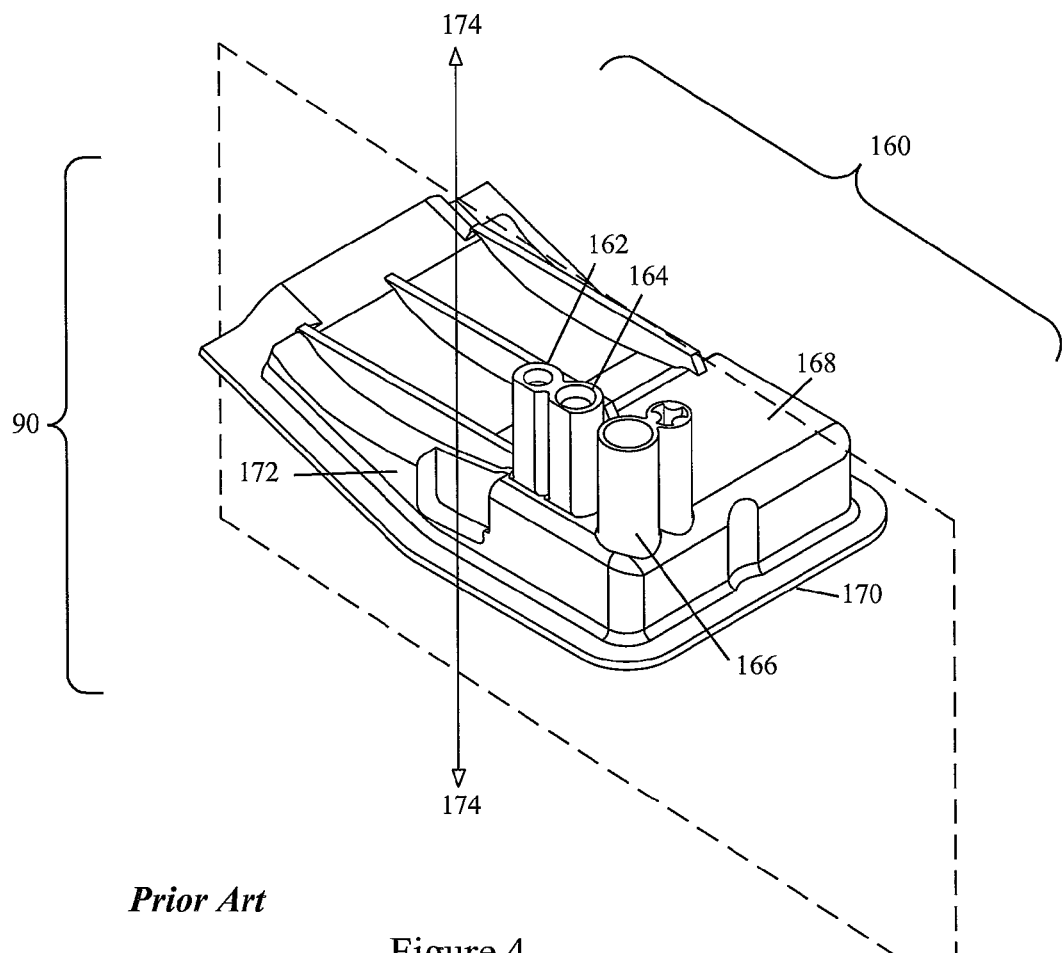
FIG. 4 is a perspective view of the optical cell of FIG. 3.

FIG. 4 provides a perspective view of an optical cell 90 for monitoring blood processing via density centrifugation, as described in U.S. Pat. No. 7,605,388. The present invention comprises improvements to such an optical cell. The illustrated prior-art optical cell 90 comprises a blood component extraction chamber 160, a first extraction port 162, a second extraction port 164 and a third extraction port 166. Extraction chamber 160 comprises a first side wall 168 and a second side wall 170 which define a blood separation region 172, wherein blood components are separated along separation axis 174 on the basis of density upon formation of a centrifugal field by a density centrifuge. In the embodiment shown in FIG. 4, extraction chamber 160, first extraction port 162 and second extraction port 164, are each capable of passing at least a portion of light scattered by blood or blood components in blood separation region 172, first extraction port 162, or second extraction port 164. Blood components of different densities are extracted through different extraction ports because first, second and third extraction ports 162, 164 and 166 are in fluid communication with different regions of blood separation region 172 during blood processing.

Figure 5:
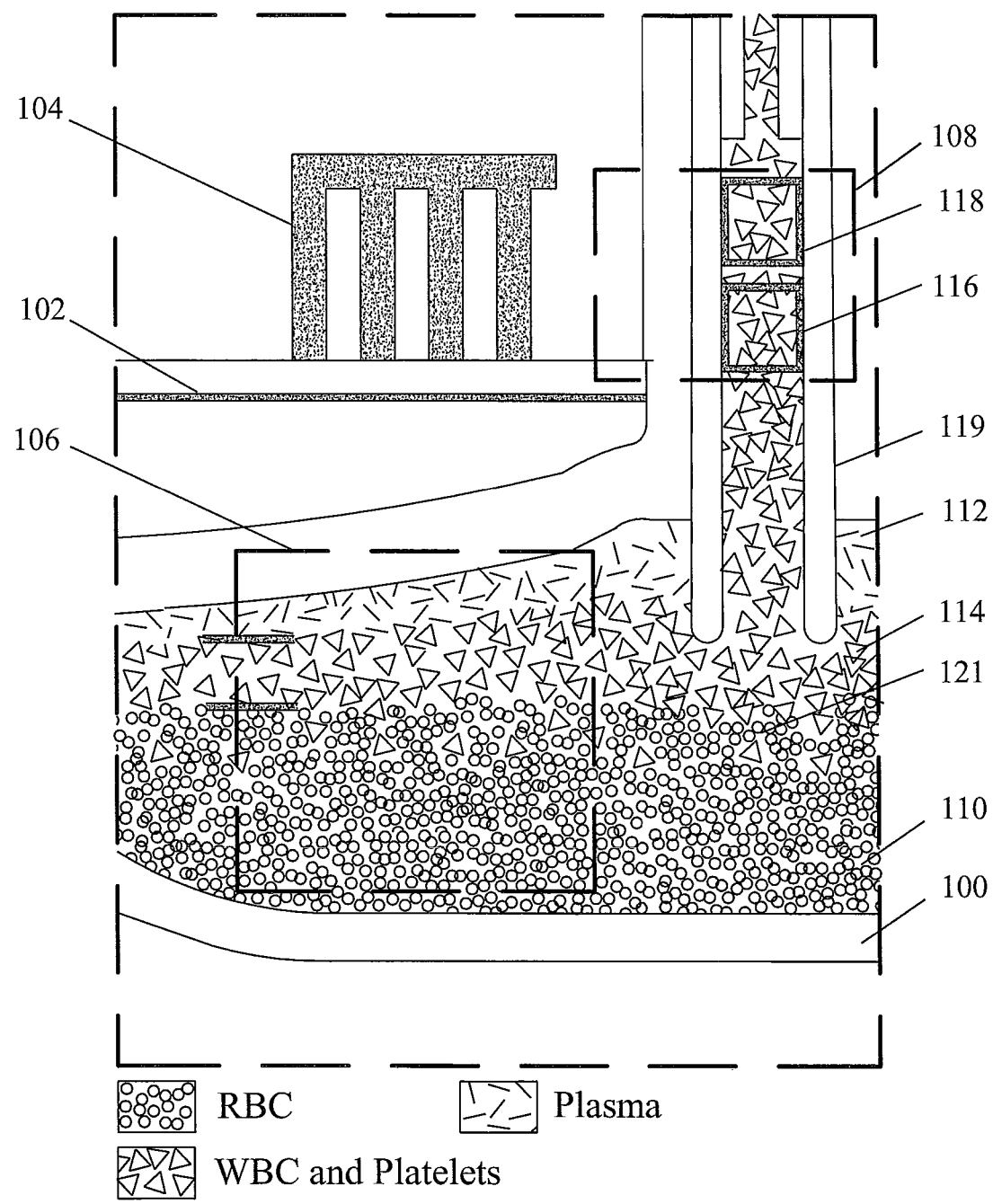
FIG. 5 is an illustration of an observation area, showing a part of the optical cell of FIG. 3.

As described in U.S. Pat. No. 7,605,388, optical cell 90 is configured such that white blood cells can be extracted through first extraction port 162, plasma and/or platelets can be extracted through second extraction port 164, and red blood cells can be extracted through third extraction port 166. As also mentioned in U.S. Pat. No. 7,605,388, optical cells of separation chambers can include one or more dams positioned proximate to the extraction ports to facilitate selective extraction of separated blood components having reduced impurities arising from adjacent components. As mentioned above, the use of dams in blood processing via density centrifugation is known in the art and described in U.S. Pat. Nos. 6,053,856; 6,334,842 and 6,514,189. FIG. 5 shows the observation region 100 focused on the optical cell 90 of the separation chamber 20. The image in FIG. 5 includes a phase boundary monitoring region 106 and a white blood cell extraction port monitoring region 108 of the optical cell. Visible in phase boundary monitoring region 106 are a red blood cell containing component 110, a plasma component 112 and a mixed phase buffy coat layer 114 having both white blood cells and platelets. The edge 102 of the optical cell comprises a first calibration marker for determining the absolute position of phase boundaries between optically differentiable blood components. The second calibration marker 104 is useful for optimizing the focusing of the light collection element and indicating the positions and physical dimensions of a phase boundary region 106 and white blood cell extraction port monitoring region 108. White blood cell extraction port monitoring region 108 includes a first flux monitoring region 116 and a second flux monitoring region 118 positioned on white blood cell extraction port 119 of the optical cell. In this example from U.S. Pat. No. 7,605,308, extraction port 119 has an orifice 121 configured to collect white blood cells in the human blood sample and extends a distance along the separation axis such that it terminates proximate to the buffy coat layer in the rotating separation chamber.

Figure 6:
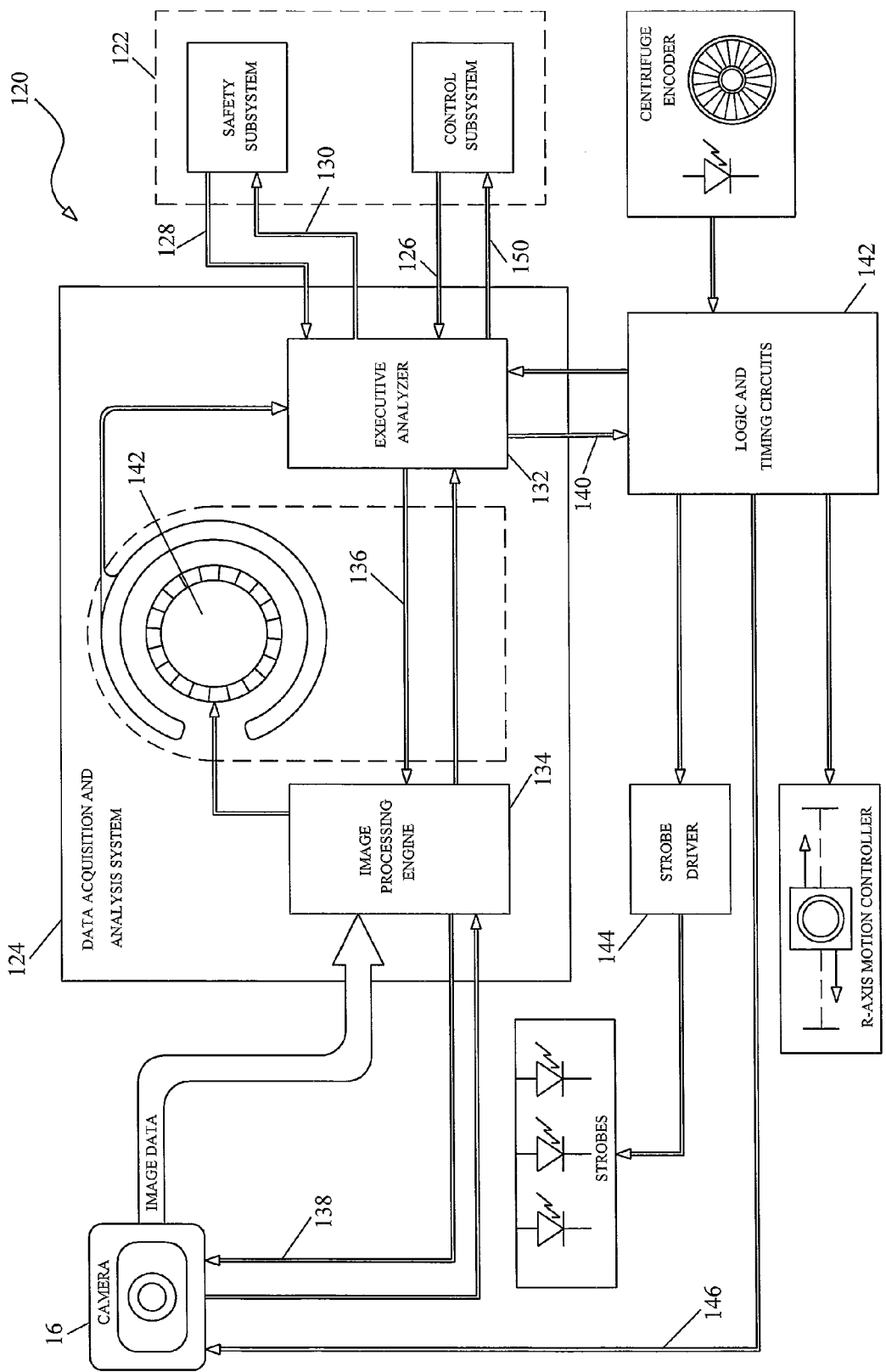
FIG. 6 shows a schematic of an exemplary control system capable of controlling blood processing.
Figure 7:
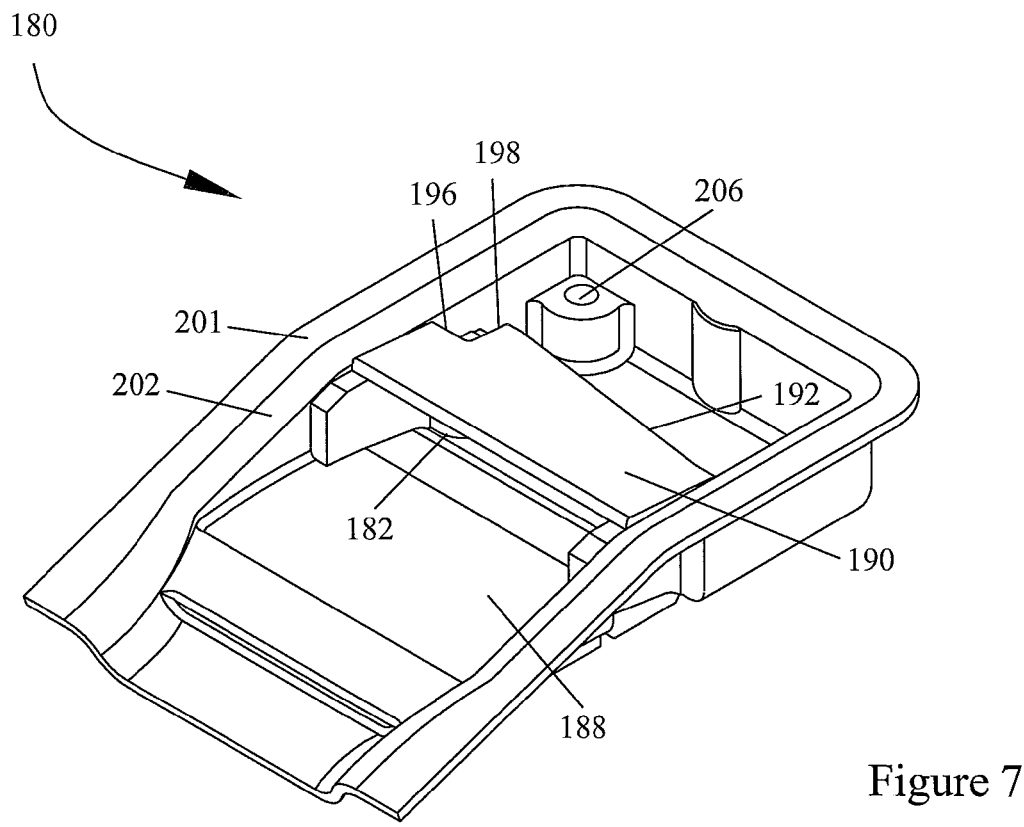
FIG. 7 is a perspective view of an optical cell of the present invention with an outer wall removed.
Figure 11:
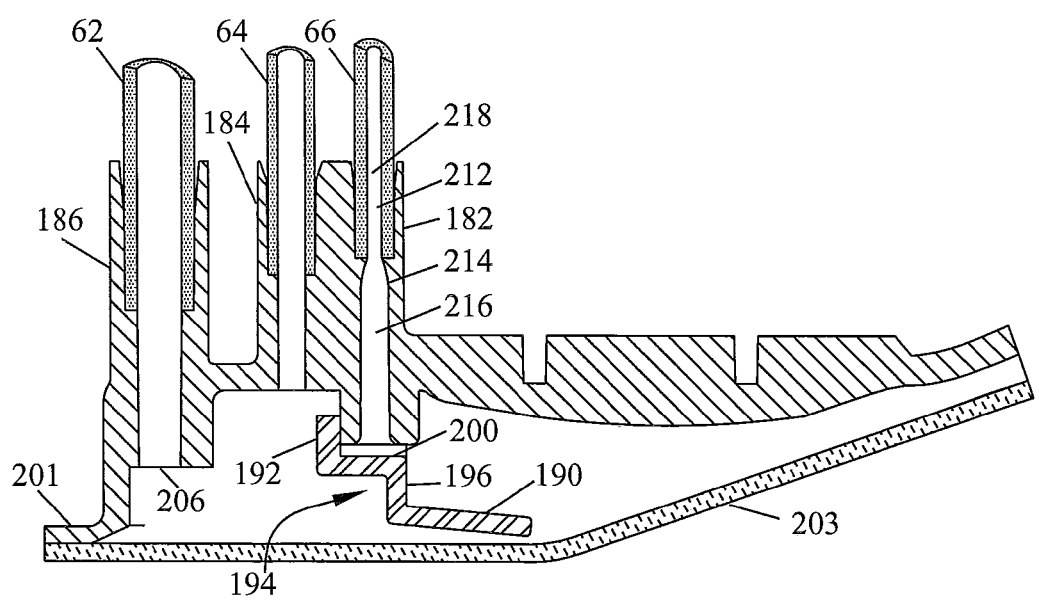
FIG. 11 is a sectional view of the optical cell taken along line 11-11 of FIG. 8.
Figure 9:
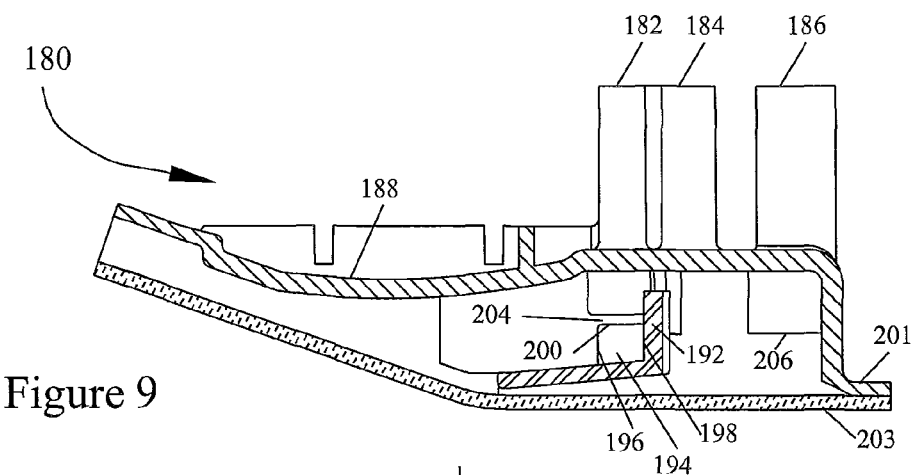
FIG. 9 is a sectional view of the optical cell taken along line 9-9 of FIG. 8. The outer wall is shown in section.
Figure 8:
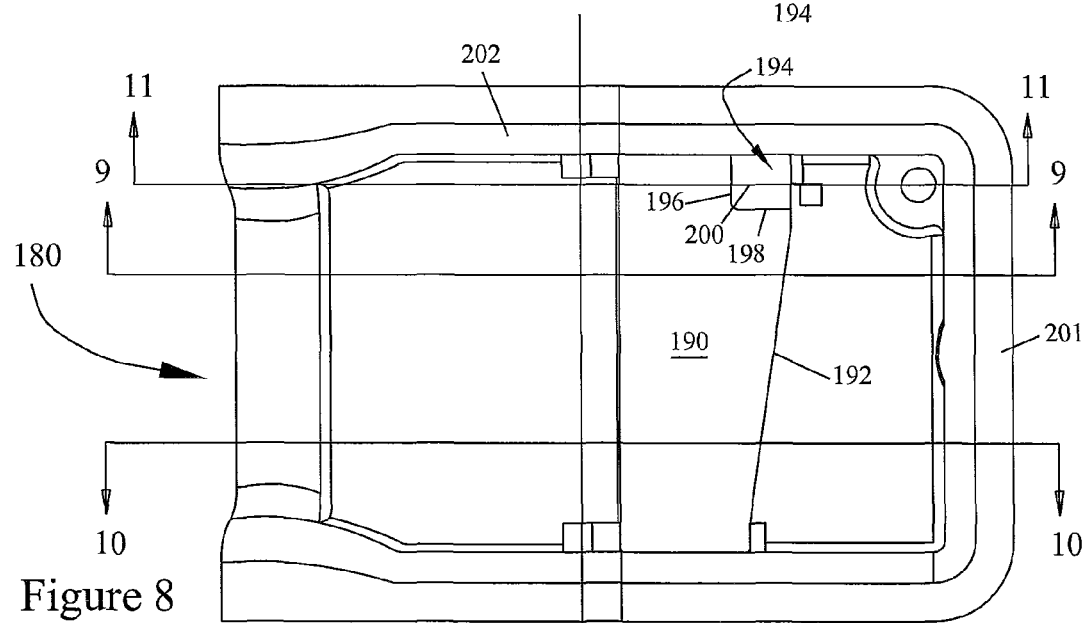
FIG. 8 is a plan view of the optical cell of FIG. 7.
Figure 10:
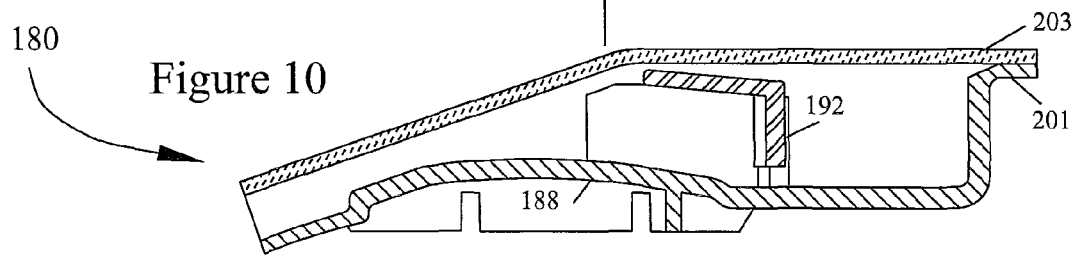
FIG. 10 is a sectional view of the optical cell taken along line 10-10 of FIG. 8.

The intensity of light transmitted through the first and second flux monitoring regions 116 and 118 depends on the concentration, spatial distribution, and cell-type of cellular material exiting the separation chamber. Light intensities transmitted through first and second flux monitoring regions 116 and 118 are acquired as a function of time and analyzed to characterize the composition and flux of cellular material out of the separation chamber. As cellular material, such as white blood cells and red blood cells, absorbs and scatters light from the light sources, passage of cellular material through the extraction port was observed to decrease the observed transmitted light intensities. FIG. 6 shows a schematic of a process control system for the blood processing device 10. The exemplary control system 120 illustrated in FIG. 6 comprises master Procedure Control system 122 in two way communication with a data acquisition and analysis system 124. Master Procedure Control system 122 is capable of receiving input signals corresponding to a selected blood processing procedure, a sample undergoing processing, or a patient undergoing treatment. Based on these input signals, Procedure Control System 122 generates and transmits procedure requests and procedure commands 126 to the smart slave data acquisition and analysis system 124. The master Procedure Control system 122 also generates and transmits a series of test commands 128 to smart slave data acquisition and analysis system 124. Data acquisition and analysis system 124 is capable of receiving test commands 128 and generating test response signals 130 which verify that the control system 120 is fully functional and that the patient or blood sample identified by the data acquisition and analysis system 124 is correctly associated with the selected blood processing procedure or therapy.

The data acquisition and analysis system 124 comprises a first computer processor 132 in two-way communication with a second computer processor 134. First computer processor 132 is configured to receive procedure requests and procedure commands 126 from master Procedure Control system 122 and transmit processing commands 136 to second computer processor 134. Second computer processor 134 analyzes the processing commands 136 and transmits camera setting commands 138 to the CCD camera and light collection element 16 which provide information related to establishing the proper exposure time, camera and light collection element position, field of view, color or monochrome imaging and other parameters necessary for acquiring high quality images of the blood processing device. First computer processor 132 is also configured to transmit illumination control and triggering commands 140 to light source and camera triggering hardware 142. Using centrifuge positional encoder data, the triggering hardware 142 transmits electronic trigger signals to the light source driver circuits 144 and camera trigger 146. Camera 16 measures light intensities comprising images of the observation region 100 on the blood processing device. The raw image data is transmitted to the second computer processor 134 for image formatting and real time image processing. In a density centrifuge, an image is acquired upon every second rotation of the separation chamber. For a rotational velocity of 3000 rotations per minute, this corresponds to acquisition of an image every 40 milliseconds.

The formatted image data is operated on by second computer processor 134 using one or more image-processing algorithms, which extract measurements from the image data and determine information about physical and chemical characteristics of the blood components undergoing processing and the operation of the blood processing device itself.

Immediately after creation of a new image data object, it is placed onto a linked list of image data objects designated as the image data list 148. This list stores image data information backwards in time. For an acquisition rate of 25 frames per second, 25 image data objects are inserted onto the image data list every second. The image data list acts as a managed circular buffer by deleting the oldest image data off the tall end of the list while inserting newly acquired image date at the head of the list.

Image data objects in the image data list are periodically examined by the first computer processor 132 and provide key data sets for monitoring and controlling blood processing. Measurements generated from the operation of the image-data analysis algorithms establish the basis of image information output signals 150 sent to the master Procedure Control system 122 and also serve as the basis of output signals sent to the camera 16, light sources, and camera triggering hardware 142 to optimize the quality of the images acquired an analyzed.

Centrifugation device controllers are capable of selective adjustment of the position of one or more phase boundaries along the separation axes. For example, centrifugation device controllers may adjust the position of phase boundaries by varying the flow rates of one or more selected blood components out of the separation chamber. This can be achieved through the use of pumps, such as peristaltic pumps, to effectuate movement through tubing. Inlet pumps can be provided which are capable of forcing material out of the separation chamber. The centrifugation device controller is capable of shutting down the centrifuge upon receiving signals indicating a leak of blood components out of the separation chamber, a misalignment of the separation chamber, a clot in the extraction ports or similar condition. The centrifuge controller is capable of regulating the infusion of a blood agent, such as an anti-coagulating agent, to the blood sample undergoing processing. Alternatively, the centrifugation device controller comprises a means for controlling the pumping rate of material out of the separation chamber in a manner capable of blowing out clots in the extraction ports. For example, upon receiving an image indicating a platelet clot in a plasma extraction port, a centrifuge device controller is capable of automatically clearing the clot by lowering the red blood cell level by reducing the pumping rate of the plasma pump and then rapidly accelerating the pumping rate of the plasma pump to force the clot out of the extraction port. Alternatively, the centrifuge controller is capable of selectively adjusting the rotational velocity of the centrifuge.

Improved Optical Cell

Although the centrifuge controller and optical system can be effective in controlling the operation of a centrifuge blood processing system, as described above, it has been found that certain transient conditions can cause loss of certain blood components, particularly white blood cells. Improvements to the optical cell 90, as described above have been found to improve the efficiency of white blood cell collection.

A function of the centrifuge blood processing system described herein may be the collection of white blood cells. It may be desired, for example, to collect white blood cells of a patient undergoing chemotherapy for cancer, so that the patient's own white blood cells can be re-infused into the patient after a chemotherapy session. White cells comprise a relatively small part of whole blood and are intermediate in density between plasma and red blood cells. The optically controlled blood processing system collects white cells by controlling the location of interfaces between plasma, buffy coat (which contains white cells and platelets), and plasma such that the buffy coat can be removed from the separation vessel 20 through the first extraction port 162 for further processing in the filtration chamber 82. In the prior art, the opening of the third (red blood cell) extraction port 166 was generally placed near the outer wall of the optical chamber, so as to be deep within the red cell layer. Such a configuration is very effective for the collection of red blood cells. It has been found, however, that the collection of white blood cells is highly sensitive to changing flow conditions. That is, if the Procedure Control System 122 stops the pumps controlling fluid flow (see above for exemplary reasons for stopping the pumps), it has been found that the interface between the red blood cells and the buffy coat generally falls, at least temporarily, to the level of the red blood cell extraction port. In such circumstances, a layer of white cells that had been collected on top of the red blood cell layer is frequently carried into the red blood cell extraction port and returned to the patient or donor. Since such white cells are co-mingled with the total blood volume of the patient/donor, they are no longer available for collection without significant re-processing of the patient's blood. Such losses can significantly decrease the efficiency of white blood cell collection.

An optical cell 180 for improved white cell extraction is illustrated in FIGS. 7 through 11. The optical cell 180 comprises a first or buffy coat extraction port 182, a second or plasma extraction port 184, and a third or red blood cell extraction port 186. When mounted on the rotor of a centrifuge blood separation device, the extraction ports extend radially inwardly toward the axis of rotation of the rotor. Upstream from the extraction ports, a curved surface 188 forms a nozzle that accelerates blood components passing through the separation chamber 20 towards the extraction ports. Downstream from the curved surface 188, white cells collect above (that is, closer to the axis of rotation) the layer of red blood cells. A ramp 190, a dam 192 and a shield 194 direct white blood cells towards the first extraction port 182. The ramp 190 is a generally planar sheet that rises gradually towards axis of rotation, lifting the RBC layer and the white cell-containing buffy coat as the blood components approach the first extraction port. The dam 192 intersects the ramp 190 and slants downstream towards the extraction port. The action of blood components flowing around the separation bag 20 direct the white cells towards the first extraction port 182. The shield 194 comprises two walls 196, 198 that connect with each other and the ramp 190, the dam 192 and a bottom wall 202 of the optical cell 180. A plate 200 caps the two walls 196, 198 and faces the first extraction port 182, leaving a small gap 204 between the plate 200 and the first extraction port 182.

The third or red blood cell extraction port 186 extends into the optical cell 180 a sufficient radial distance from the axis of rotation along a separation axis such that an orifice 206 lies between the plate 200 and the ramp 190, as measured radially from the axis of rotation along a separation axis. The third extraction port 186 is spaced circumferentially downstream from the first extraction port 182.

The optical cell 180 has a lip 201 that faces radially outwardly when the separation vessel 20 is mounted in the rotor of the blood separator. The lip 201 is sealed to a flexible outer wall 203 of the separation vessel. Under the influence of centrifugal forces created by the rotor, the outer wall 203 conforms to the shape of a groove in the rotor, thereby creating a space between the ramp 190 and the wall 203. Concentrated red blood cells pass beneath the ramp 190 and accumulate behind the ramp 190, dam 192, and shield 194, where the red blood cells can be extracted through the red blood cell extraction port 186.

This configuration allows white cell-containing buffy coat to be withdrawn from the optical cell through the first extraction port for further separation in the filtration chamber 82. If the flow conditions are interrupted, for example, by stopping one or more of the pumps, the RBC level falls to the level of the orifice 206 of the RBC extraction port 186. The dam and ramp, however, prevent the buffy coat layer and white cells from flowing downstream to the third extraction port, thus preserving the white cells for collection when steady state flow conditions are re-established.

A further feature of the optical cell 180 reduces false detection of red blood cells in the first extraction port 182, a condition that would cause the Procedure Control System 122 to pause the pumps, which might cause a loss of collectable white cells. As shown in FIG. 3, the prior art first extraction port 162 comprised a stepped lumen 208 having a larger diameter bore radially outwardly and a smaller diameter bore radially inwardly, with a lip 210 between the two areas. The larger diameter bore radially outward is needed to allow for a sufficiently large area for optical detection of conditions in the flux monitoring regions 116, 118. The smaller diameter radially inward is needed to promote a higher flow velocity through the white cell tube 66. The volume of white cells collected is comparatively small, compared to the volumes of red blood cells or plasma being processed through the system. A narrow lumen in the white cell tube 66 reduces the possibility of stagnation in the white cell line. Nevertheless, it is believed that vortices in the fluid flowing through the lumen 208 in the prior art design of FIG. 3 may temporarily capture white blood cells or cellular aggregates. White cells may continue to accumulate in the vicinity of the lip until a critical volume is dislodged and passes through the small diameter area of the lumen. The accumulation of white cells near the flux monitoring regions 116, 118, impedes the transmission of light through the flux monitoring regions. The darkening of these regions may be erroneously interpreted by the Procedure Control System 122 as red blood cells. Corrective action by the Procedure Control System may interrupt the collection of white cells or may cause the pumps to be paused needlessly. To alleviate this condition, a lumen or bore 212 in the first extraction port 182 (see FIG. 11) has a frustro-conical taper 214 from a first downstream region 216 having a first diameter toward a second upstream region 218 having a second diameter as defined by the lumen of the white cell tube 66.

The improved separation chamber 20 and optical cell 180 thus provide more efficient collection of white cells by reducing false detection of red blood cells and associated changes in flow conditions and by preventing white cell loss when flow conditions are changed.

We claim:

1. An optical cell for a separation chamber of a density centrifuge blood processing system for separating fluid components, said optical cell being adapted to be mounted on a rotor of said blood processing system, said optical cell comprising:
    an extraction chamber adapted to transmit at least a portion of an incident optical beam; and
    a first extraction port extending radially outwardly into said optical cell with respect to an axis of rotation of said rotor and being adapted to transmit at least a portion of the incident optical beam, said first extraction port having
        an orifice opening into said extraction chamber,
        a bore for passing fluid components, said bore being adjacent said orifice of said first extraction port, said bore having a first diameter,
        a lumen in fluid communication with said bore and downstream therefrom with respect to fluid flowing through said bore into said lumen, said lumen having a second diameter smaller than said first diameter of said bore, and
        a frustro-conical passageway smoothly coupling said first diameter of said bore to said second diameter of said lumen.

2. A tubing set for a density centrifuge blood processing system for separating fluid components, said tubing set comprising
    a separation chamber adapted to be mounted on a rotor of said blood processing system,
    an optical cell in fluid communication with said separation chamber, said optical cell comprising:
        an extraction chamber adapted to transmit at least a portion of an incident optical beam; and
        a first extraction port extending radially outwardly into said optical cell with respect to an axis of rotation of said rotor and being adapted to transmit at least a portion of the incident optical beam, said first extraction port having
            an orifice opening into said extraction chamber,
            a bore for passing fluid components, said bore being adjacent said orifice of said first extraction port, said bore having a first diameter,
            a lumen in fluid communication with said bore and downstream therefrom with respect to fluid flowing through said bore into said lumen, said lumen having a second diameter smaller than said first diameter of said bore, and
            a frustro-conical passageway smoothly coupling said first diameter of said bore to said second diameter of said lumen.

3. A centrifugal blood separation system comprising
    a rotor adapted to impart centrifugal force to separate blood into blood components,
    a light source adapted to selectively illuminate an observation region on said rotor,
    an optical sensor adapted to detect light from said light source,
    a control system in electrical communication with said rotor, said light source and said optical sensor and adapted to control said rotor, light source and sensor,
    a separation vessel mounted on said rotor, wherein blood may be separated into blood components,
    an optical cell in fluid communication with said separation vessel, said optical cell comprising:
        an extraction chamber adapted to transmit at least a portion of an incident optical beam; and
        a first extraction port extending radially outwardly into said optical cell with respect to an axis of rotation of said rotor and being adapted to transmit at least a portion of the incident optical beam, said first extraction port having
            an orifice opening into said extraction chamber,
            a bore for passing fluid components, said bore being adjacent said orifice of said first extraction port, said bore having a first diameter,
            a lumen in fluid communication with said bore and downstream therefrom with respect to fluid flowing through said bore into said lumen, said lumen having a second diameter smaller than said first diameter of said bore, and
            a frustro-conical passageway smoothly coupling said first diameter of said bore to said second diameter of said lumen.

* * * * *